United States Patent [19]

Siuta-Mangano

[11] Patent Number: 4,795,629

[45] Date of Patent: Jan. 3, 1989

[54] CROSSLINKING OF HAIR THIOLS USING CYSTAMINE

[75] Inventor: Patricia Siuta-Mangano, Valley Cottage, N.Y.

[73] Assignee: Chesebrough-Pond's Inc., Greenwich, Conn.

[21] Appl. No.: 74,206

[22] Filed: Jul. 16, 1987

Related U.S. Application Data

[63] Continuation-in-part of Ser. No. 069,929, Jul. 6, 1987.

[51] Int. Cl.$^4$ ............................ A61K 7/00; A61K 7/06
[52] U.S. Cl. ........................................ 424/70; 424/47; 514/544; 514/569; 530/388; 530/390; 530/391
[58] Field of Search .................. 514/544, 569; 424/47, 424/70; 564/69; 530/388, 390, 391

[56] References Cited

U.S. PATENT DOCUMENTS

| | | | |
|---|---|---|---|
| 3,862,221 | 1/1975 | Kalopissis et al. | 564/192 |
| 3,882,114 | 5/1975 | Kalopissis et al. | 424/70 |
| 3,902,507 | 9/1975 | Kinney et al. | 424/71 |
| 3,957,774 | 5/1976 | Kalopissis et al. | 424/70 |
| 4,349,532 | 9/1982 | Vanlerberghe | 424/47 |
| 4,666,941 | 5/1987 | Shroot et al. | 514/544 |
| 4,738,841 | 4/1988 | Pigiet | 424/71 |
| 4,751,286 | 6/1988 | Packard et al. | 530/388 |

OTHER PUBLICATIONS

Sagarin, E.; "Cosmetics, Science & Technology", vol. 2, p. 230 (1972); Wiley Interscience.

Zviak, C.; "Science of Hair Care", vol. 7, pp. 183–212, Marcel Dekker, Inc. (1986), Series Entitled Dermatology.

*Primary Examiner*—Ellis P. Robinson
*Assistant Examiner*—P. J. Ryan
*Attorney, Agent, or Firm*—Melvin H. Kurtz

[57] ABSTRACT

Keratinous material, such as human hair, in which disulfide linkages have been ruptured to form sulfhydryl groups can be set using cystamine.

7 Claims, No Drawings

CROSSLINKING OF HAIR THIOLS USING CYSTAMINE

CROSS REFERENCE TO RELATED APPLICATION

This application is a continuation-in-part of application Ser. No. 069,929, filed July 6, 1987, in the name of P. Siuta-Mangano entitled CROSSLINKING REAGENTS USEFUL IN TREATING HAIR.

The present invention relates to the treatment of keratinous materials to effect improvements in permanent waving or straightening.

BACKGROUND OF THE PRESENT INVENTION

Keratinous material, which occurs in animal hair such as camel hair, mohair, wool, horsehair, cattle hair, fur and the like, and feathers, such as from poultry and, in particular, human hair consists of long polypeptide chains crosslinked to one another by means of occasional disulfide linkages. The disulfide linkages act to hold the hair in a disulfide linkages permits the polypeptide chains to function independently, allowing for the deformation of the shape of the hair without elasticity. Rupture of disulfide linkages may be accomplished by the use of various reducing agents, such as inorganic sulfides, sulfites, hydrosulfites and cyanides, mercaptans, thioglycolic acids, and various other compounds. Sulfhydryl groups are formed in place of the disulfide linkages.

In the cold-waving of hair, reduction of the disulfide linkages in hair is commonly performed in order to produce a permanent set, as in permanent waving, curling, or de-kinking of hair. The shaping of hair has conventionally been carried out by contracting the hair with a reducing agent in the form of liquids, creams, or gels while the hair has been mechanically formed into the desired new shape. The reducing composition is applied to the hair for a sufficient time to allow shaping to occur by the reductive disruption of the disulfide linkages. The reducing composition is then washed from the hair, and the normal resilience of the hair may then be regained by restoring the crosslinkages either by means of oxidizing agents or by treatment with the various crosslinking agents.

The restoration of the disulfide linkages is important in order to increase tensile strength, as well as remove the sulfhydryl groups as reactive sites. The desired crosslinking may be obtained by oxidation, as by heating in the presence of hair or by reacting with hydrogen peroxide solution. Bromates are frequently employed as oxidizing agents in the setting of permanently waved hair. Valuable properties may also be secured by the use of crosslinking agents, such as alkylene dihalides or dihalocarboxylic acids (U.S. Pat. No. 2,739,033) or dimaleimides (U.S. Pat. No. 2,850,351). By the use of crosslinking agents, it is possible to convert sulfhydryl linkages to cross linkages.

If permanent straightening of the hair is desired, the reducing lotion is generally applied in a thickened form such as, for instance, in a cream, and evenly distributed throughout the hair by combing. The hair is combed more or less continuously and maintained in a straightened condition for a period of time sufficient to allow rupture of the disulfide linkages. The shaping agent is then washed out with water and the set is then fixed as with an oxidizing agent or a crosslinking agent.

Many of the crosslinking agents which have been proposed heretofore are not water-soluble and must be used in the form of emulsions. Some of these agents are toxic and thus difficult to employ. Others are voltaile and present a hazard to people using the same.

Other crosslinking reagents not encumbered by the difficulties of past reagents are desirable.

BRIEF SUMMARY OF THE INVENTION

In accordance with the present invention, it has been found that keratinous materials in which disulfide linkages have been ruptured by the action of a reducing agent can be treated to restore cross linkages between keratin molecules by the application of an amount of cystamine sufficient to effect the desired treatment.

While a wide group of keratinous fiber can be treated in accordance with the present invention, including animal hair such as camel hair, mohair, wool, horsehair, cattle hair, hog bristles and the like; and feathers, such as from chicken, duck, turkey and the like, the invention is particularly directed to waving human hair whether in vivo or in vitro, i.e., in the form of wigs. The invention is particularly directed to "cold waving" and hair straightening systems and will be discussed in connection therewith.

DETAILED DESCRIPTION OF THE INVENTION

The reducing agents most commonly used in cold waving hair lotions for rupturing cystine linkages are thiols or mercaptans as well as sulfites and/or bisulfites. A number of mercaptans can only provide acceptable efficiency at high pH whereas others with a lower pK and a high ionization constant can be effective at lower pH levels. For example, the ammonium salt of thiogyloclic acid can provide acceptable waving efficiency (reduction) if the pH of the solution exceeds 9. Other compounds such as thioglycolamides or clygol thioglycolates, sulfites and/or bisulfites can be used at neutral or even slightly acidic pH. The following are mercaptans and thiols which have commonly been used in cold waving lotions: thioglycolic acid, thiolactic acid, cysteine, thioglycerol, thioglycolic hydrazide, thioglycolamide, glycerol monothioglycolate, beta-metcaptopropionic acid, N-hydroxyethyl mercapto-acetamide, N-methyl mercapto-acetamide, beta-mercapto-ethylamine, beta-metcaptopropionamide, 2-mercapto-ethanesulfonic acid, dimercaptoadipic acid, dithiothreitol, homocysteinethiolactone, cystein derivatives, and polythiol derivatives formed by the addition of cysteamine onto a maleic anhydridealkylvinylether copolymer. The sulfites and/or bisulfites which can be used are those normally used in hair waving such as the sodium and ammonium salts. The amount of the reducing agent used is that sufficient to rupture a sufficient number of disulfide bonds for effective hair waving or hair straightening as would be appreciated by one of ordinary skill in the art.

By the breaking of the disulfide bonds to form free sulfhydryl groups pendent on the hair, the hair can be formed or shaped as desired such as by winding on rollers or pins, or combed out as in the case of hair straightening. The breaking of the disulfide bonds is generally accomplished in accordance with the usual practice, which involved applying the reducing agent to the hair wound on curlers. Heat can be provided at this point.

The deformed hair, while curled or straightened, is then wetted with a crosslinking composition containing the crosslinking reagent of the invention in water or in a carrier or base such as a lotion or cream, preferably buffered. The crosslinking reagent is preferably water soluble or made water soluble by known techniques. The carriers are of known types and are similar to those presently in use in waving and "neutralizing" compositions. The water or carrier desirable holds the crosslinking reagent in contact with the hair for a period of time sufficient to effect permanent setting of the hair. Generally the cystamine is used in a concentration ranging from about 0.1% to about 10% weight per volume. The crosslinking reagent is applied under conditions conductive to effecting crosslinking. A pH of between about 6 and about 9 (less than that which would cause permanent breakdown of the hair protein) has been found effective for that purpose using the compound of the invention.

The crosslinking reagent is preferably applied to the hair in a buffered system, and particularly a buffered system designed to maintain the pH between about 6 and about 9, and preferably between about 7 and about 8. Any or a combination of alkali metal phosphates, acetates, borates and the like which are non-reactive with the crosslinking reagent to thus destroy crosslinking sites, can be used to maintain the pH of the hair treated with the crosslinking composition within the range specified. Any pH effects caused by the reducing agent can be offset by thorough washing of the hair with water prior to the application of the crosslinking composition.

The crosslinking composition can also contain a wetting agent or surfactant which is non-reactive with the crosslinking reagent or the hair to destroy crosslinking sites. The surfactant can be anionic, such as soaps. and alkyl sulfates, such as sodium dedecyl sulfate; cationic such as quaternary ammonium compounds; nonionic, such as glycol esters, glycerol esters, sorbitan esters, polyoxyalkalene esters, polyoxyalkalene ethers, and modified lanolin, as well as amphoteric surfactants. The surfactant is used in an amount sufficient to assist in wetting the hair with the crosslinking reagent. The amount depending on the efficiency of the surfactant.

The crosslinking reagents can be applied to the hair alone after reduction or in combination with a reducing agent that is compatible with the crosslinking reagent. The use of the single-step system allows for the reduction and immediate crosslinking of the sulfydryl groups.

The hair is treated for a period of time sufficient to effect the crosslinking to provide the curl and, in some instances, tensile strength increases desired. Illustrative times include from about 3 minutes to any practical non-deterioration of the hair, upper limit though lesser times can be used if lesser effect on the hair is desired.

The crosslinking reagent is preferably applied in aqueous solution at a temperature between the ranges of about 10° C. (50° F.) and 93° C. (200° F.). Time of treatment may vary within wide limits depending on the temperature of the solution, the particular reducing and crosslinking agents used, and the nature of the keratinous material being treated.

The hair can be further treated with presently used neutralizing agents and crosslinking reagents in order to oxidize any free SH groups to disulfide linkages as would be appreciated by one of ordinary skill in the art. The oxidizing or neutralizing chemicals used can be any of the oxidizing agents capable of restoring the disulfide linkages in the hair keratin during the resetting stage, such as aqueous solution of hydrogen peroxide, alkali metal bromates, alkali metal perborates, urea hydrogen peroxide, sodium sesquicarbonate, etc. Rinsing alone with water may restore the broken linages as well, but it will be much slower.

The permanent waving system of the invention can be designed for professional and home application. The system and its compositions can contain ingredients normal to such compositions. Fragrance compounds, coloring agents, thickening agents, opacifying agents, sequestering agents, solubilizing agents, gelling agents, conditioning agents, etc., may be added to compositions of this invention in amounts conventionally used in hair waving and straightening compositions. Any compound which will react with the crosslinking reagent to remove or neutralize reactive sites thereon is preferably avoided. These ingredients are fully outlined in The Science of Hair Care, edited by Charles Zviak, Vol. 7 of a series entitled Dermatology, Marcel Dekker, Inc. 1986, which is incorporated herein by reference.

As used herein, the term "% weight per volume" is intended to means "grams per 100 milliliters".

The present invention is more fully illustrated in the Examples which follow.

All neutralization (reoxidation), unless otherwise stated, was performed using the neutralizer provided with the commercial waving lotion used in the examples for 5 minutes. All rinsing was performed with running water for 2 minutes. All times are in minutes.

EXAMPLE 1

Swatches (0.5 grams; 20.3 centimeters in length) of European brown Caucasian hair wrapped around curling rods with an central diameter of 1.27 centimeters were treated with a commercially available waving lotion (Clariol ® Professional Kind to Hair Perm System) for 20 minutes to rupture the disulfide bonds. These swatches were then rinsed for 2 minutes with running tap water. Some swatches were treated with 10 milliliters of a crosslinking solution containing about 2.5% weight per volume cystamine crosslinking reagent in 200 millimolar sodium phosphate buffer (pH 8.5) with 1 millimolar EDTA at a final pH of about 7.5 for 20 minutes. The tresses were rinsed again under running tap water. Some samples were further treated with the neutralizing lotion accompanying the commercial waving lotion in order to oxidze any free SH groups. The Clairol ® Perm System control was neutralized using the neutralizer provided with the commercial hair waving system for 5 minutes followed by a water rinse. The buffer treatment without cystamine and without neutralization was conducted for 20 minutes.

Hair swatches cut to 17.8 centimeters were analyzed for hanging curl length immediately after unrolling the hair swatches, after 2 hours of gentle drying, after 1 hour of soaking in 4 liters of tap water containing a few drops of 29% sodium dodecyl sulfate, and after another 2 hours of drying. The lengths were compared during the fifth hour, i.e., the final drying state. Curl lengths comparable to that obtained using the commercial hair waving system with neutralization (Clairol ® Perm System) were seen with cystamine and no neutralization. Hair swatches treated with buffer alone, i.e., no crosslinking reagent, for 20 minutes and no neutralization gave very little curl.

The following results, which are the average of two experiments, were obtained. The data are reported in centimeters of hanging hair, the data for solution being measurements made while the curl was in the solution. A reduction in length is an indication of the degree of curl.

TABLE 1

|  | Curl Length (centimeters) | | | |
| --- | --- | --- | --- | --- |
|  | Wet 0 hr. | Dry 2 hr. | Solution 1 hr. | Dry 2 hr. |
| Control Commercial Waving System With Neutralization | 13.0 | 13.7 | 3.8 | 15.7 |
| Cystamine Without Neutralization | 10.4 | 13.0 | 2.5 | 15.7 |
| Buffer Without Neutralization | 13.7 | 13.7 | 5.1 | 16.5 |

The above treated swatches were analyzed for luster, silky feel and combability. Cystamine gave appearance results comparable with or better than the commercial lotion-treated hair or untreated hair, e.g., better looking curls, more luster, and more silkiness than the commercially treated hair swatches.

EXAMPLE 2

Example 1 was repeated with the following changes. The cystamine was used in an amount of 5% weight per volume in 200 millimolar phosphate buffer with 1 millimolar EDTA, final pH 7.4; one sample was treated with cystamine for 12 minutes, rinsed with water then neutralized using the neutralizer from the commercial waving system and rinsed with water; the buffer treatment after disulfide bond severing was conducted for 12 minutes, rinsed and one sample was subsequently neutralized with the commercial neutralizer followed by a water rinse. The following results were obtained:

TABLE 2

|  | Curl Length (centimeters) | | | |
| --- | --- | --- | --- | --- |
|  | Wet 0 hr. | Dry 2 hr. | Solution 1 hr. | Dry 2 hr. |
| Control Commercial Waving System With Neutralization | 13.2 | 14.7 | 2.5 | 15.7 |
| Cystamine Without Neutralization | 12.7 | 14.5 | 11.2 | 15.7 |
| Cystamine With Neutralization | 12.4 | 14.2 | 3.0 | 15.2 |
| Buffer Without Neutralization | 16.3 | 16.0 | 8.6 | 16.8 |
| With Neutralization | 13.7 | 14.7 | 3.8 | 15.7 |

EXAMPLE 3

Swatches of hair (as defined in Example 1) were treated on a curler. For control, a hair sample was contacted for 20 minutes with a commercial waving lotion (Clairol ® Perm System) to rupture disulfide bonds, rinsed in flowing tap water, neutralized, i.e., reoxidized, utilizing the neutralizer accompanying the commercial waving system, and rinsed. A second group of hair was treated with a commercial waving lotion (Clairol ® Perm System) for 20 minutes to rupture disulfide bonds, rinsed in flowing tap water, treated with 10 milliliters of a crosslinking solution of cystamine in an amount of 2.5% weight per volume in 200 millimolar sodium phosphate buffer and 1 millimolar EDTA (pH 8.5) for 20 minutes (final pH 78.5), rinsed in running tap water, neutralized, and rinsed. A third set was treated the same as in the preceding procedure, except that no crosslinking reagent in the buffer was used.

The following results were obtained:

TABLE 3

|  | Curl Length (centimeters) | | | |
| --- | --- | --- | --- | --- |
|  | Wet 0 hr | Dry 2 hr. | Solution 1 hr. | Dry 2 hr. |
| Control Commercial Waving System, Neutralized | 13.3 | 14.0 | 2.6 | 14.6 |
| Cystamine, Neutralized | 12.7 | 14.0 | 2.5 | 14.6 |
| Buffer, Neutralized | 12.7 | 14.0 | 3.2 | 14.6 |

Single tagged hair strands were analyzed for tensile properties including break point, maximum elongation before break, and total work. A decrease of from 2% to 12% in tensile properties was noted over the control. Optimization of the system may avoid these decreases.

What is claimed is:

1. A process for treating keratinous material in which disulfide linkages have been ruptured to form sulfhydryl groups by the action of a reducing agent which comprises contacting said keratinous material with cystamine in a carrier at a pH in the range of from about 6 to about 9 to crosslink sulfhydryl groups.

2. The process as claimed in claim 1 wherein the keratinous material is human hair.

3. The process as recited in claim 1 wherein the cystamine is used in an amount effective to crosslink an amount of sulfhydryl groups sufficient to set the keratinous material.

4. The process as recited in claim 1 wherein the cystamine is used in a concentration ranging from about 0.1% to about 10% weight per volume.

5. A process which comprises treating hair with a reducing agent until a substantial portion of disulfide groups of the hair are converted to sulfhydryl groups and, while maintaining the hair in a fixed position, contacting the hair with cystamine in an amount and under conditions sufficient to set the hair.

6. A process which comprises contacting human hair, while the hair is mechanically maintained in a suitable condition of curl, with an amount of a reducing agent capable of rupturing disulfide linkages in the hair and a hair setting amount of cystamine.

7. The method of claim 6 wherein the human hair is simultaneously contacted with the reducing agent and cystamine.

* * * * *